(12) United States Patent
Yamaguchi et al.

(10) Patent No.: US 9,492,689 B2
(45) Date of Patent: Nov. 15, 2016

(54) WATER-IN-OIL EMULSION SUNSCREEN COSMETIC COMPOSITION

(75) Inventors: Kazuhiro Yamaguchi, Yokohama (JP); Sawako Ishitobi, Yokohama (JP)

(73) Assignee: Shiseido Company, Ltd., Tokyo (JP)

( * ) Notice: Subject to any disclaimer, the term of this patent is extended or adjusted under 35 U.S.C. 154(b) by 0 days.

(21) Appl. No.: 13/575,043

(22) PCT Filed: Jan. 13, 2011

(86) PCT No.: PCT/JP2011/000153
§ 371 (c)(1),
(2), (4) Date: Jul. 25, 2012

(87) PCT Pub. No.: WO2011/093018
PCT Pub. Date: Aug. 4, 2011

(65) Prior Publication Data
US 2012/0288458 A1 Nov. 15, 2012

(30) Foreign Application Priority Data
Jan. 26, 2010 (JP) .................. 2010-013772

(51) Int. Cl.
*A61K 8/06* (2006.01)
*A61Q 17/04* (2006.01)
*A61K 8/37* (2006.01)
*A61K 8/41* (2006.01)
*A61K 8/49* (2006.01)

(52) U.S. Cl.
CPC ............ *A61Q 17/04* (2013.01); *A61K 8/064* (2013.01); *A61K 8/37* (2013.01); *A61K 8/41* (2013.01); *A61K 8/4946* (2013.01)

(58) Field of Classification Search
CPC ........ A61Q 17/04; A61K 8/064; A61K 8/37; A61K 8/41; A61K 8/4946
USPC .......................................... 424/60, 59, 401
See application file for complete search history.

(56) References Cited

U.S. PATENT DOCUMENTS

| 4,940,577 | A | * | 7/1990 | Greenberg ............ A61K 8/064 424/59 |
| 6,153,174 | A | | 11/2000 | Sperling et al. |
| 2006/0008440 | A1 | * | 1/2006 | Blatt et al. ............... 424/70.14 |
| 2007/0104676 | A1 | | 5/2007 | Moser et al. |
| 2007/0292676 | A1 | | 12/2007 | Naigertsik et al. |
| 2009/0017081 | A1 | | 1/2009 | Takakura et al. |
| 2009/0041817 | A1 | | 2/2009 | Takakura et al. |
| 2010/0291011 | A1 | | 11/2010 | Ikebe et al. |

FOREIGN PATENT DOCUMENTS

| DE | 19849514 | 5/2000 |
| DE | 102007005334 | 8/2008 |
| EP | 2002822 | 12/2008 |
| JP | 10-120543 | 5/1998 |
| JP | 2003-104824 | 4/2003 |
| JP | 2006-528944 | 12/2006 |
| JP | 2007-175405 | 7/2007 |
| JP | 2007-217379 | 8/2007 |
| JP | 2007-217380 | 8/2007 |
| JP | 2007-217393 | * 8/2007 ............ A61K 8/891 |
| JP | 2009-196896 | 9/2009 |
| WO | 2004/082580 A2 | 9/2004 |
| WO | 2005/009604 | 2/2005 |
| WO | 2009/020067 | 2/2009 |

OTHER PUBLICATIONS

Angus Alkanolamines in Sun Protection Products: retrieved from internet: http://www.dow.com/scripts/litorder.asp?filepath=angus/pdfs/noreg/319-00062.pdf. Retrieved on Mar. 7, 2013.*
Octyl Methoxycinnamate: retrieved from internet: http://en.wikipedia.org/wiki/Octyl_methoxycinnamate. Retrieved on Mar. 7, 2013.*
Octyl methoxycinnamate—OMCX: retireved from internet:http://www.kyowa.eu/files/pdfs/Octyl_Methoxycinnamate_(OMCX).pdf. Retrieved on Mar. 25, 2015.*
Chemical UVB+UVA sunscreen/sunblock: octocrylene: retrieved form internet: http://www.smartskincare.com/skinprotection/sunblocks/sunblock_octocylene.html. Retrieved on Mar. 25, 2015.*
MSDS of octocrylene: retrieved from internet: https://www.spectrumchemical.com/MSDS/O0116.PDF. Retrieved on Mar. 25, 2015.*
Octocrylene: retrieved from internet: https://www.karebaybio.com/products/octocrylene-14730.html. Retrieved on Oct. 9, 2015.*
English Abstract of JP 10-120543 published May 12, 1998, one page.
English Abstract of JP 2007-217379, published Aug. 30, 2007, one page.
English Abstract of JP 2007-217380, published Aug. 30, 2007, one page.
English Abstract of JP 2007-217393, published Aug. 30, 2007, one page.
English Abstract of JP 2006-528944, published Dec. 28, 2006, one page.
English Abstract of DE 19849514, published May 4, 2000, one page.
English Abstract of JP 2009-196896, published Sep. 3, 2009, one page.
English Abstract of JP 2003-104824, published Apr. 9, 2003, one page.
English Abstract of JP 2007-175405, published Jul. 12, 2007, one page.

(Continued)

*Primary Examiner* — Brian-Yong Kwon
*Assistant Examiner* — Hong Yu
(74) *Attorney, Agent, or Firm* — Rankin, Hill & Clark LLP

(57) ABSTRACT

A water-in-oil type sunscreening cosmetic material containing phenylbenzimidazole sulfonic acid, 2-amino-2-methyl-1,3-propanediol and/or 2-amino-2-(hydroxymethyl)propane-1,3-diol, and octyl methoxycinnamate.

2 Claims, No Drawings

(56) References Cited

OTHER PUBLICATIONS

Burnett, et al. "Final Amended Report on Safety Assessment on Aminomethyl Propanol and Aminomethyl Propanediol", International Journal of Toxicology, vol. 28, No. 6S, pp. 141S-161S, 2009, twenty-one pages.
International Search Report, Application No. PCT/JP2011/000153, dated Mar. 8, 2011, two pages.
Japanese Office Action dated Mar. 27, 2012 and partial English translation, 6 pages.
Japanese Office Action dated Jun. 26, 2012 and partial English translation, 3 pages.
Anonymous, "Sun Care Cream Ultra Protection", GNPD; Mintel; Nov. 1, 2005, XP002680719, 5 pages.
Database GNPD [Online] "Perfect Essence Sunscreen", XP002713280, Mar. 1, 2010, 3 pages.
European Search Report, Application No. 11736735.9, dated Oct. 24, 2013, 6 pages.
Taiwanese Office Action dated Aug. 11, 2014 issued in the corresponding Taiwanese patent application No. 100102509; Partial English translation thereof.
European Office Action issued in corresponding EP Application No. 11736735.9 mailed May 20, 2014, three pages.

\* cited by examiner

WATER-IN-OIL EMULSION SUNSCREEN COSMETIC COMPOSITION

TECHNICAL FIELD

The present invention relates to water-in-oil emulsion type sunscreening cosmetic materials.

BACKGROUND ART

It is conventional to add a UV absorber or a UV scattering agent (e.g., zinc oxide, titanium dioxide) to a sunscreening cosmetic material in order to intercept the irradiation of the skin with ultraviolet light to thereby attain a high sun protection factor (SPF) value. For instance, Patent Literature 1 discloses a sunscreening cosmetic material containing octyl triazone and phenylbenzimidazole sulfonic acid in combination. In Patent Literature 2, the present applicant has proposed a water-in-oil emulsion type sunscreening cosmetic material composed of octocrylene, hydrophobicized titanium dioxide and/or zinc oxide, phenylbenzimidazole sulfonic acid and a salt formed by neutralizing phenylbenzimidazole sulfonic acid, as a material effective at shielding against ultraviolet light and highly stable in prevention/suppression of deterioration in smell with time.

The above mentioned phenylbenzimidazole sulfonic acid is one of few effective UV absorbers becoming water-soluble if neutralized with sodium hydroxide or triethanolamine into a salt, and is suitably blended in a water-containing cosmetic material. Phenylbenzimidazole sulfonic acid as a general-purpose UV absorber nevertheless has a problem in that discoloration occurs with time if the acid is used for a water-in-oil type sunscreening cosmetic material in combination with a hydrophobicized UV scattering agent (e.g., zinc oxide, titanium dioxide). In order to solve the problem, the present applicant has proposed in Patent Literature 3 a water-in-oil emulsion type sunscreening cosmetic material containing hydrophobicized titanium oxide and/or zinc oxide, phenylbenzimidazole sulfonic acid, triethanolamine, and trimethyl siloxysilicate in adjusted amounts.

Ultraviolet light is classified by wavelength into three types, ultraviolet A (UVA) at 320 to 400 nm, ultraviolet B (UVB) at 290 to 320 nm, and ultraviolet C (UVC) at 290 nm or below. Since most of UV absorbers are effective in a specified wavelength range, attempts are made to add two or more UV absorbers to a water-in-oil emulsion type sunscreening cosmetic material aiming at absorption of ultraviolet light in a wide range from UVA to UVB, and expecting the improvement in UV protection effect owing to the combined use of different UV absorbers.

In recent years, diethylamino hydroxybenzoyl hexyl benzoate and bis-ethylhexyloxyphenol methoxyphenyl triazone have been developed as a UVA absorber, and octyl triazone as a UVB absorber. Such substances are solid at room temperature, and need to be dissolved in an ester oil or a cinnamate UV absorber (such as octyl methoxycinnamate) in liquid form upon blending.

CITATION LIST

Patent Literature

Patent Literature 1: Japanese Unexamined Patent Publication No. 10(1998)-120543
Patent Literature 2: Japanese Unexamined Patent Publication No. 2007-217379
Patent Literature 3: Japanese Unexamined Patent Publication No. 2007-217380

SUMMARY OF INVENTION

Technical Problems

When the present inventors obtained a phenylbenzimidazole sulfonate salt by neutralization with triethanolamine and combined the salt with octyl methoxycinnamate as dissolved in an ester oil, so as to prepare a water-in-oil emulsion type sunscreening cosmetic material, it was found that deterioration in smell occurs with time. In the case of a phenylbenzimidazole sulfonate salt formed by neutralization with sodium hydroxide, the emulsion stability was found to be decreased, although with no deterioration in smell.

The present invention was made under the circumstances as above, having an object of providing a water-in-oil emulsion type sunscreening cosmetic material containing phenylbenzimidazole sulfonic acid and octyl methoxycinnamate that involves no deterioration in smell and is excellent in emulsion stability.

Solution to Problems

The water-in-oil type sunscreening cosmetic material of the present invention comprises phenylbenzimidazole sulfonic acid, 2-amino-2-methyl-1,3-propanediol and/or 2-amino-2-(hydroxymethyl)propane-1,3-diol, and octyl methoxycinnamate.

It is preferable that the water-in-oil type sunscreening cosmetic material of the invention contains not less than 10 wt % of an ester oil component. It is more preferable that the inventive material contains 0.1 to 10 wt % of an ultraviolet A absorber.

It is also preferable that the water-in-oil type sunscreening cosmetic material of the present invention contains essentially no perfume. In this regard, "containing essentially no perfume" refers to "having no perfume added thereto on purpose," that is to say, does not refer to "not containing even a natural perfume derived from any raw material for the water-in-oil type sunscreening cosmetic material."

Advantageous Effects of Invention

The water-in-oil type sunscreening cosmetic material of the present invention which comprises phenylbenzimidazole sulfonic acid, 2-amino-2-methyl-1,3-propanediol, and octyl methoxycinnamate is rid of deterioration in smell and made excellent in emulsion stability by the neutralization of phenylbenzimidazole sulfonic acid with 2-amino-2-methyl-1,3-propanediol and/or 2-amino-2-(hydroxymethyl)propane-1,3-diol into a salt.

Addition of 0.1 to 10 wt % of a UVA absorber allows the absorption of ultraviolet light in a wide range from UVA to UVB, and combination of a UVA absorber with phenylbenzimidazole sulfonic acid and octyl methoxycinnamate makes it possible to obtain a water-in-oil type sunscreening cosmetic material with an improved UV protection effect.

The water-in-oil type sunscreening cosmetic material of the invention, as being rid of deterioration in smell, can be obtained as a fragrance-free one containing essentially no perfume.

DESCRIPTION OF EMBODIMENTS

The water-in-oil type sunscreening cosmetic material of the present invention is characterized in that it contains phenylbenzimidazole sulfonic acid, 2-amino-2-methyl-1,3-propanediol (hereafter also referred to as AMPD) and/or 2-amino-2-(hydroxymethyl)propane-1,3-diol (hereafter also referred to as Tris, as normally abbreviated), and octyl methoxycinnamate. AMPD and Tris are neutralizers for phenylbenzimidazole sulfonic acid, and phenylbenzimidazole sulfonic acid will be water-soluble if neutralized with AMPD or Tris. As a result, an offensive smell is prevented and a good emulsion stability is attained even though the acid is combined with octyl methoxycinnamate as an ester UV absorber.

The ratio of phenylbenzimidazole sulfonic acid to AMPD and/or Tris preferably ranges from 4:1 to 2:1, and more preferably from 3:1 to 2:1. A ratio of phenylbenzimidazole sulfonic acid to AMPD falling outside the range of 4:1 to 2:1 is unfavorable because of an inadequate neutralization. The content of phenylbenzimidazole sulfonic acid in the water-in-oil type sunscreening cosmetic material is 0.01 to 5 wt %, preferably 0.1 to 4 wt %, and more preferably 0.4 to 3 wt % based on the total amount of the material. An adequate UV protection effect is not exerted with a phenylbenzimidazole sulfonic acid content lower than 0.01 wt %, while a content higher than 5 wt % is unfavorable because the material may be made sticky or the acid which is too much in amount to be completely dissolved may be crystallized. AMPD and Tris may be used alone or in combination with each other. The content of AMPD and/or Tris (their total content in the case of combined use) in the material is 0.01 to 2.5 wt %, preferably 0.025 to 2 wt %, and more preferably 0.2 to 1.5 wt %.

Preferably, the water-in-oil type sunscreening cosmetic material of the invention is caused to contain a UVA absorber so that the material can absorb ultraviolet light in a wider range, with the UVA absorber content being 0.1 to 10 wt %, especially 1 to 5 wt %. An adequate UV protection effect is not exerted with a UVA absorber content lower than 0.1 wt %, while a content higher than 10 wt % is unfavorable because the material may be made sticky or the UVA absorber which is too much in amount to be completely dissolved may be crystallized. Suitable UVA absorbers are exemplified by diethylamino hydroxybenzoyl hexyl benzoate, as well as bis-ethylhexyloxyphenol methoxyphenyl triazine and methylene bis-benzotriazolyl tetramethylbutylphenol also effective for the absorption in a UVB wavelength range. Such substances may be used alone, or two or more out of them may be used in an appropriate combination.

The above UVA absorbers are solid at room temperature, and need to be dissolved in an ester oil or octyl methoxycinnamate upon blending. If any of the UVA absorbers as such is combined with phenylbenzimidazole sulfonic acid as neutralized with triethanolamine or sodium hydroxide, an offensive smell is given off or the emulsion stability is decreased. The water-in-oil type sunscreening cosmetic material of the invention, in which AMPD is used as a neutralizer, avoids an offensive smell and is excellent in emulsion stability even though the UVA absorber as above and phenylbenzimidazole sulfonic acid are used in combination for the material.

Octyl methoxycinnamate contained in the water-in-oil type sunscreening cosmetic material of the invention is an oil-soluble UV absorber in liquid form, and is included in an ester oil component of the material. The ester oil component including octyl methoxycinnamate preferably comprises not less than 10 wt %, more preferably 10 to 80 wt %, and even more preferably 15 to 50 wt % of the total material. If the ester oil component amount is less than 10 wt %, a stable emulsification is not possible. On the other hand, an ester oil component amount more than 80 wt % lessens the water to be blended, which makes the material give inadequately refrigerant feeling.

The water-in-oil emulsion type sunscreening cosmetic material of the present invention may contain another oil-soluble UV absorber in liquid form apart from octyl methoxycinnamate and the UVA absorber as described above. Specific examples include octocrylene (2-ethylhexyl 2-cyano-3,3-diphenyl acrylate), octyl salicylate, homomenthyl salicylate, dimethicodiethyl-benzal malonate, and methyl bis(trimethylsiloxy)silylisopentyl trimethoxycinnamate. Such substances may be used alone, or two or more out of them may be used in an appropriate combination. Combination of different UV absorbers allows the absorption of ultraviolet light in a wide range and the improvement in UV protection effect owing to the combined use.

The total amount of the oil-soluble UV absorbers in liquid form, including octyl methoxycinnamate and the UVA absorber, to be blended in the water-in-oil type sunscreening cosmetic material is preferably 0.3 to 15 wt %, and more preferably 1 to 10 wt % based on the total amount of the material. An adequate UV protection effect is not exerted if the oil-soluble UV absorbers in liquid form are blended in a total amount lower than 0.3 wt %. On the other hand, a total amount higher than 15 wt % is unfavorable because UV absorbers contained in a formulation in such an amount may make the formulation sticky.

Apart from the ingredients as described above, the water-in-oil type sunscreening cosmetic material of the invention may appropriately contain a conventional cosmetic ingredient as long as it does not impair the object and effects of the present invention. Exemplary ingredients include water-soluble polymers, oil-soluble polymers, polymer powder, emulsifiers, waxes, alcohols, liquid fats and oils, ester oils (other than octyl methoxycinnamate), hydrocarbon oils, silicone oils, fatty acids, higher alcohols, fatty acid esters, drugs, UV absorbers (excluding phenylbenzimidazole sulfonic acid, octyl methoxycinnamate, and the UVA absorber as described above), UV scattering agents, and organically modified clay minerals.

The water-soluble polymers include homopolymers and copolymers of 2-acrylamido-2-methylpropane sulfonic acid (hereafter abbreviated as "AMPS"). The copolymers are those with comonomers such as vinyl pyrrolidone, amide acrylate, sodium acrylate, and hydroxyethyl acrylate. In other words, the water-soluble polymers are exemplified by an AMPS homopolymer, a vinyl pyrrolidone/AMPS copolymer, a dimethyl acrylamide/AMPS copolymer, an amide acylate/AMPS copolymer, and a sodium acrylate/AMPS copolymer.

In addition, a carboxyvinyl polymer, ammonium polyacrylate, sodium polyacrylate, a sodium acrylate/alkyl acrylate/sodium methacrylate/alkyl methacrylate copolymer, carrageenan, pectin, mannan, curdlan, chondroitin sulfuric acid, starch, glycogen, gum arabic, sodium hyaluronate, tragacanth gum, xanthan gum, mucoitin sulfuric acid, hydroxyethyl guar gum, carboxymethyl guar gum, guar gum, dextran, keratosulfate, locust bean gum, succinoglucan, chitin, chitosan, carboxymethyl chitin, and agar are mentioned as an example.

The oil-soluble polymers are exemplified by trimethylsiloxy silicic acid, alkyl-modified silicone, and polyamide-modified silicone.

The polymer powder is exemplified by a dimethicone crosspolymer, a (dimethicone/vinyl dimethicone) crosspolymer, polymethyl silsesquioxane, polyethylene, and methyl polymethacrylate.

The waxes are exemplified by beeswax, candelilla wax, carnauba wax, lanolin, liquid lanolin, and jojoba wax.

Exemplary emulsifiers include silicone surfactants, glycerin fatty acid esters, polyglycerin fatty acid esters, polyoxyethylene glycerin fatty acid esters, sorbitan fatty acid esters, and polyoxyethylene sorbitan fatty acid esters, with the preferred being silicone surfactants.

No particular limitation is imposed on the silicone surfactant to be contained, so that any silicone surfactant usable in a material of a water-in-oil emulsion type is available. Examples include a poly(oxyethylene/oxypropylene) methylpolysiloxane copolymer, a polyoxyethylene methylpolysiloxane copolymer, a silicone chain branched-type methylpolysiloxane copolymer, an alkyl chain branched-type polyoxyethylene methylpolysiloxane copolymer, an alkyl chain/silicone chain branched-type polyoxyethylene methylpolysiloxane copolymer, crosslinked polyoxyethylene methylpolysiloxane, alkyl group-containing, crosslinked polyoxyethylene methylpolysiloxane, branched-type polygricerin-modified silicone, crosslinked, polygricerin-modified silicone, alkyl group-containing, crosslinked, polygricerin-modified silicone, and alkyl group branched-type polygricerin-modified silicone.

The alcohols are exemplified by lower alcohols such as ethanol and isopropanol, higher alcohols such as isostearyl alcohol, octyldodecanol and hexyldecanol, and polyhydric alcohols such as ethylene glycol, propylene glycol, 1,3-butylene glycol, dipropylene glycol and polybutylene glycol.

The liquid fats and oils are exemplified by avocado oil, camellia oil, turtle oil, macadamia nut oil, corn oil, mink oil, olive oil, rapeseed oil, egg yolk oil, sesame oil, persic oil, wheat germ oil, sasanqua oil, castor oil, linseed oil, safflower oil, cotton seed oil, perilla oil, soybean oil, peanut oil, tea seed oil, Japanese nutmeg oil, rice bran oil, China wood oil, Japanese tung oil, jojoba oil, germ oil, and triglycerin.

The ester oils are exemplified by isopropyl myristate, cetyl octanoate, octyl dodecyl myristate, isopropyl palmitate, butyl stearate, hexyl laurate, myristyl myristate, cetyl oleate, decyl oleate, hexyl decyl dimethyloctanoate, cetyl lactate, myristyl lactate, lanolin acetate, isocetyl stearate, isocetyl isostearate, isononyl isononanoate, cholesteryl 12-hydroxystearate, ethylene glycol di-2-ethylhexanoate, a dipentaerythritol fatty acid ester, N-alkyl glycol monoisostearate, neopentyl glycol dicaprate, diisostearyl malate, glycerin di-2-heptylundecanoate, trimethylolpropane tri-2-ethylhexanoate, trimethylolpropane triisostearate, pentaerythritol tetra-2-ethylhexanoate, glycerin tri-2-ethylhexanoate, glycerin trioctanoate, glycerin triisopalmitate, trimethylolpropane triisostearate, cetyl 2-ethylhexanoate, 2-ethylhexyl palmitate, glycerin trimyristate, glyceride tri-2-heptylundecanoate, a castor oil fatty acid methyl ester, oleyl oleate, acetoglyceride, 2-heptylundecyl palmitate, diisobutyl adipate, 2-octyldodecyl N-lauroyl-L-glutamate ester, di-2-heptylundecyl adipate, ethyl laurate, di-2-ethylhexyl sebacate, 2-hexyldecyl myristate, 2-hexyldecyl palmitate, 2-hexyldecyl adipate, diisopropyl sebacate, 2-ethylhexyl succinate, and triethyl citrate.

The hydrocarbon oils are exemplified by liquid petrolatum, ozocerite, squalane, pristane, paraffin, ceresin, squalene, petrolatum, microcrystalline wax, polyethylene wax, and Fischer-Tropsch wax.

The silicone oils are exemplified by dimethylpolysiloxane, octamethyl siloxane, decamethyl tetrasiloxane, methyl hydrogen polysiloxane, methylphenyl polysiloxane, hexamethyl cyclotrisiloxane, octamethyl cyclotetrasiloxane, and decamethyl cyclopentasiloxane.

The fatty acids are exemplified by lauric acid, myristic acid, palmitic acid, stearic acid, behenic acid, and arachidonic acid.

The higher alcohols are exemplified by lauryl alcohol, myristyl alcohol, cetyl alcohol, stearyl alcohol, behenyl alcohol, arachyl alcohol, batyl alcohol, chimyl alcohol, carnaubyl alcohol, ceryl alcohol, koryanyl alcohol, myricyl alcohol, lacceryl alcohol, elaidyl alcohol, isostearyl glyceryl ether, octyl alcohol, triacontyl alcohol, serachyl alcohol, cetostearyl alcohol, oleyl alcohol, lanolin alcohol, hydrogenated lanolin alcohol, hexyldecanol, and octyldecanol.

The fatty acid esters are exemplified by myristyl myristate, cetyl palmitate, cholesteryl stearate, and beeswax fatty acid 2-octyldodecyl.

The drugs are exemplified by L-ascorbic acid and its salt derivatives, glycyrrhizic acid and its derivatives such as dipotassium glycyrrhizate and monoammonium glycyrrhizate, glycyrrhetinic acid and its derivatives such as stearyl glycyrrhetinate, allantoin, tranexamic acid and its salt derivatives, alkoxysalicylic acid and its salt derivatives, glutathione and its salt derivatives, allantoin, and azulene.

Examples of the UV absorbers excluding phenylbenzimidazole sulfonic acid, octyl methoxycinnamate and the UVA absorber as described before include cinnamic acid derivatives such as isopropyl methoxycinnamate and isoamyl methoxycinnamate; para-aminobenzoic acid (hereafter abbreviated as "PABA") and PABA derivatives such as ethyl PABA, ethyl dihydroxypropyl PABA, ethylhexyl dimethyl PABA, and glyceryl PABA; salicylic acid derivatives such as dipropylene glycol salicylate and TEA salicylate; benzophenone derivatives such as benzophenone-1, benzophenone-2, benzophenone-3 or oxybenzone, benzophenone-4, benzophenone-5, benzophenone-6, benzophenone-8, benzophenone-9, and benzophenone-12; benzylidene camphor derivatives such as 3-benzylidene camphor, 4-methylbenzylidene camphor, benzylidene camphor sulfonic acid, camphor benzalkonium methosulfate, terephthalylidene dicamphor sulfonic acid, and polyacrylamidomethyl benzylidene camphor; triazine derivatives such as anisotriazine, ethylhexyl triazone, diethylhexyl butamido triazone, and 2,4,6-tris(diisobutyl 4'-aminobenzalmalonate)-s-triazine; phenylbenzimidazole derivatives such as disodium phenyldibenzimidazole tetrasulfonate; phenylbenzotriazole derivatives such as drometrizole trisiloxane and methylene bis(benzotriazolyl tetramethylbutylphenol); anthranilic derivatives such as menthyl anthranilate; imidazoline derivatives such as ethylhexyl dimethoxybenzylidene dioxoimidazoline propionate; benzalmalonate derivatives such as polyorganosiloxanes with benzalmalonate functional groups; and 4,4-diarylbutadiene derivatives such as 1,1-dicarboxy(2,2'-dimethylpropyl)-4,4-diphenylbutadiene.

The UV scattering agents are exemplified by hydrophobicized inorganic pigments such as titanium dioxide and zinc oxide.

The organically modified clay minerals are exemplified by quaternary ammonium salt cation-modified clay minerals.

The water-in-oil emulsion type sunscreening cosmetic material of the present invention may be prepared into a product in emulsion form or a product in cream form. Such products can be manufactured in a usual manner by mixing the indispensable ingredients and the conventional cosmetic ingredients as described above.

EXAMPLES

Following the procedure below, the sunscreening cosmetic materials as examples of the present invention and comparative examples were prepared according to the recipes as set forth in Table 1 (figures in Table 1 referring to parts by weight). A neutralizer was initially added to a water-soluble UV absorber (phenylbenzimidazole sulfonic acid) to cause their reaction, then water, an alcohol, and a humectant were added and homogeneously dispersed so as to prepare the aqueous phase component. On the other hand, the remaining ingredients including oil-soluble UV absorbers were added to the oil component to disperse them homogeneously. To the resultant dispersion, the aqueous phase component containing the water-soluble UV absorber that had been prepared in advance was gradually added to thereby prepare a sunscreening cosmetic material of a water-in-oil emulsion type.

Evaluation Methods (UV Protection Effect)

In accordance with the "SPF Measurement Standards" (revised version, 2007) as set up by the Japan Cosmetic Industry Association, samples of Example 2 as well as Comparative Examples 1 and 2 were measured in SPF value.

(Smell Deterioration Suppressing Effect)

Samples of the individual examples were caused to stand still at 40° C. for one month, then used actually by a panel of women (n=10) so as to evaluate them for the smell upon application. The sample which was not deteriorated in smell was evaluated as "good," and the sample which gave off an offensive smell was evaluated as "offensive smell."

(Emulsion Stability)

Samples of the individual examples were caused to stand still at 40° C. for one month, then observed under an optical microscope. The sample whose emulsified particles were uniform with no coalescence or aggregation was evaluated as "stable," and the sample which exhibited coalescence or aggregation of emulsified particles was evaluated as "coalescence."

TABLE 1

| | | Ex. 1 | Ex. 2 | Comp. Ex. 1 | Comp. Ex. 2 | Comp. Ex. 3 | Comp. Ex. 4 | Comp. Ex. 5 | Comp. Ex. 6 | Comp. Ex. 7 |
|---|---|---|---|---|---|---|---|---|---|---|
| Water | Purified water | 33.5 | 34 | 43.55 | 36.5 | 33 | 33.5 | 33 | 33.5 | 33 |
| Alcohol | Ethyl alcohol | 5 | 5 | 5 | 5 | 5 | 5 | 5 | 5 | 5 |
| Humectant | Glycerin | 3 | 3 | 3 | 3 | 3 | 3 | 3 | 3 | 3 |
| | 1,3-Butylene glycol | 3 | 3 | 3 | 3 | 3 | 3 | 3 | 3 | 3 |
| | Xylitol | 1 | 1 | 1 | 1 | 1 | 1 | 1 | 1 | 1 |
| | Tranexamic acid | 2 | 2 | 2 | 2 | 2 | 2 | 2 | 2 | 2 |
| UV absorber (water-soluble) | Phenylbenzimidazole sulfonic acid | 2.5 | 2.5 | — | — | 2.5 | 2.5 | 2.5 | 2.5 | 2.5 |
| Neutralizer | Triethanolamine | — | — | — | — | 1 | — | — | — | — |
| | Sodium hydroxide | — | — | — | — | — | 0.5 | 1 | — | — |
| | Aminomethyl propanol | — | — | — | — | — | — | — | 0.5 | 1 |
| | 2-Amino-2-methyl-1,3-propanediol | 0.5 | 1 | — | — | — | — | — | — | — |
| Oil component | Dimethylpolysiloxane | 2 | 2 | 2 | 2 | 2 | 2 | 2 | 2 | 2 |
| | Decamethyl cyclopentasiloxane | 5 | 5 | 5 | 5 | 5 | 5 | 5 | 5 | 5 |
| | Isododecane | 10 | 10 | 10 | 10 | 10 | 10 | 10 | 10 | 10 |
| | Cetyl oleate | 3 | 3 | 3 | 3 | 3 | 3 | 3 | 3 | 3 |
| | Diisopropyl sebacate | 3 | 3 | 3 | 3 | 3 | 3 | 3 | 3 | 3 |
| UV absorber (oil-soluble) | Octyl methoxycinnamate | 7.5 | 7.5 | 5 | 7.5 | 7.5 | 7.5 | 7.5 | 7.5 | 7.5 |
| | Dimethicodiethyl-benzal malonate | 3 | 3 | — | 3 | 3 | 3 | 3 | 3 | 3 |
| | Octocrylene | 3 | 3 | 5 | 3 | 3 | 3 | 3 | 3 | 3 |
| | Bis-ethylhexyloxyphenol methoxyphenyl triazine | 1 | 1 | — | 1 | 1 | 1 | 1 | 1 | 1 |
| | Diethylamino hydroxybenzoyl hexyl benzoate | 2 | 2 | — | 2 | 2 | 2 | 2 | 2 | 2 |
| | Methylene bis-benzotriazolyl tetramethylbutylphenol | 1 | 1 | 1 | 1 | 1 | 1 | 1 | 1 | 1 |
| Surfactant | Lauryl PEG-9 polydimethylsiloxyethyl dimethicone | 1 | 1 | 1 | 1 | 1 | 1 | 1 | 1 | 1 |
| Thickening agent | (Palmitic acid/2-ethylhexanoic acid) dextrin | 1 | 1 | 1 | 1 | 1 | 1 | 1 | 1 | 1 |
| Usability improving powder | Polymethyl silsesquioxane | 6 | 5 | 6 | 6 | 6 | 6 | 6 | 6 | 6 |
| Chelating agent | Sodium edetate | 0.2 | 0.2 | 0.1 | 0.2 | 0.2 | 0.2 | 0.2 | 0.2 | 0.2 |
| Stabilizer | Sodium chloride | 0.3 | 0.3 | — | 0.3 | 0.3 | 0.3 | 0.3 | 0.3 | 0.3 |
| Preservative | Phenoxyethanol | 0.5 | 0.5 | 0.35 | 0.5 | 0.5 | 0.5 | 0.5 | 0.5 | 0.5 |
| Evaluation | UV protection effect (SPF) | — | 59 | 38 | 38 | — | — | — | — | — |
| | Smell deterioration suppressing effect (40° C., 1 mth.) | Good | Good | Good | Good | Offensive smell | Good | Good | Offensive smell | Offensive smell |
| | Emulsion stability (40° C., 1 mth.) | Stable | Stable | Stable | Stable | Stable | Coalescence | Coalescence | Stable | Stable |

As seen from Table 1, each of Examples 1 and 2, which was the water-in-oil type sunscreening cosmetic material of the present invention, and had phenylbenzimidazole sulfonic acid neutralized with 2-amino-2-methyl-1,3-propanediol into a salt, was not deteriorated in smell and had a good emulsion stability. Comparative Example 3 having used triethanolamine as a neutralizer also had a good emulsion stability indeed but, at the same time, gave off an offensive smell. Comparative Examples 4 and 5 each having used sodium hydroxide as a neutralizer avoided an offensive smell, although coalescence of emulsified particles was observed, that is to say, these examples did not have a favorable emulsion stability. Comparative Examples 6 and 7 each having used aminomethyl propanol as a neutralizer had a good emulsion stability but with an offensive smell.

In addition, Example 2 had a higher SPF value than both Comparative Examples 1 and 2 which were each a water-in-oil type sunscreening cosmetic material not containing phenylbenzimidazole sulfonic acid. As evident from Examples 1 and 2, in the case of a water-in-oil type sunscreening cosmetic material containing phenylbenzimidazole sulfonic acid and octyl methoxycinnamate, deterioration in smell is suppressed and a good emulsion stability is attained by using 2-amino-2-methyl-1,3-propanediol and/or 2-amino-2-(hydroxymethyl)propane-1,3-diol as a neutralizer. Moreover, it is possible to improve the UV protection effect of such a water-in-oil type sunscreening cosmetic material because an oil-soluble UV absorber apart from octyl methoxycinnamate can be added.

In Table 2 below, exemplary recipes for the water-in-oil type sunscreening cosmetic material of the invention are set forth (figures in Table 2 referring to parts by weight). The water-in-oil type sunscreening cosmetic materials of Recipes 1 through 3 were prepared as follows: Oil-soluble UV absorbers, the oil component, a film forming agent, and a surfactant were homogeneously mixed to solution, then a thickening agent, a UV scattering agent, and powder were added and dispersed by a homomixer so as to prepare the oily phase. To ion-exchanged water, a neutralizer, then a water-soluble UV absorber were added, and the mixture was agitated until a solution was obtained. A chelating agent, a humectant, a preservative, and an alcohol were added to the solution so as to prepare the aqueous phase. The aqueous phase was added to the oily phase with agitation, and the resultant mixture was agitated by the homomixer to prepare a sunscreening cosmetic material. The sunscreening cosmetic materials thus obtained avoided an offensive smell even after the storage at 40° C. for one month or longer.

TABLE 2

| Classification | Raw material | Recipe 1 | Recipe 2 | Recipe 3 |
|---|---|---|---|---|
| Oil-soluble UV absorber | Octyl methoxycinnamate | 7 | 7.5 | 7.5 |
| | Octocrylene | — | — | 5 |
| | Diethylamino hydroxybenzoyl hexyl benzoate | 0.5 | 2 | 2 |
| | Bis-ethylhexyloxyphenol methoxyphenyl triazine | 1 | — | — |
| Water-soluble UV absorber | Phenylbenzimidazole sulfonic acid | 3 | 3 | 1.5 |
| Oil component | Dimethylpolysiloxane 1.5 cs | 3 | 5 | 20 |
| | Cycloalkylpolysiloxane | 15 | 15 | 15 |
| | Diisopropyl sebacate | — | — | 5 |
| | Cetyl 2-ethylhexanoate | 5 | — | 5 |
| | Octyl palmitate | — | — | 2 |
| | C12-15 alkyl benzoate | 5 | 5 | — |
| | Squalane | 1 | — | — |
| | Sucrose fatty acid ester mixture | — | 0.5 | 0.5 |
| Film forming agent | Trimethylsiloxy silicic acid | 3 | 5 | — |
| | Dextrin palmitate | 0.5 | — | — |
| Surfactant | Lauryl PEG-9 polydimethylsiloxyethyl dimethicone | — | — | 2 |
| | Polyoxyethylene/methylpolysiloxane copolymer | 2 | 5 | |
| Thickening agent | Dimethyl distearyl ammonium hectorite | 0.8 | 0.5 | — |
| UV scattering agent | Aluminum stearate-coated titanium oxide | 1 | — | |
| | Octyl triethoxysilane-coated particulate zinc oxide | — | 15 | 5 |
| Powder | Silicone resin powder | 5 | — | 2 |
| | Polyalkyl silsesquioxane | — | 5 | — |
| | Talc | 2 | — | — |
| | Spherical nylon powder | 1 | — | — |
| Water | Ion-exchanged water | Balance | Balance | Balance |
| Neutralizer | 2-amino-2-methyl-1,3-propanediol | 1.2 | | 0.7 |
| | 2-amino-2-(hydroxymethyl)propane-1,3-diol | | 1.2 | |
| Chelating agent | Edetate salt | q.s. | q.s. | q.s. |
| Humectant | Glycerin | 1 | — | 5 |
| | 1,3-Butylene glycol | 5 | — | — |
| | Dipropylene glycol | — | 5 | 1 |
| Drug | Oil-soluble licorice extract | 0.5 | — | — |
| | Dipotassium glycyrrhizate | 0.05 | 0.02 | 0.02 |
| | Glutathione | — | 1 | — |
| | Thiotaurine | — | 0.05 | — |

TABLE 2-continued

| Classification | Raw material | Recipe 1 | Recipe 2 | Recipe 3 |
|---|---|---|---|---|
| | Sophora angustifolia root extract | | 1 | — |
| | Ascorbic acid | | — | 0.01 |
| Preservative | Paraben | q.s. | q.s. | — |
| | Phenoxyethanol | q.s. | q.s. | — |
| Alcohol | Ethanol | 6 | — | 6 |

While 2-amino-2-methyl-1,3-propanediol or 2-amino-2-(hydroxymethyl)propane-1,3-diol was used alone in each of Examples and Recipes as above, similar results are obtained by using a combination of these substances.

The invention claimed is:

1. A water-in-oil type sunscreening cosmetic material comprising:
   0.1 to 4 wt % phenylbenzimidazole sulfonic acid,
   octyl methoxycinnamate,
   0.2 to 1.5 wt % 2-amino-2-methyl-1,3-propanediol as a neutralizer of the phenylbenzimidazole sulfonic acid,
   0.1 to 10 wt % of an ultraviolet A absorber,
   10 to 80 wt % of the octyl methoxycinnamate and an ester oil component selected from the group consisting of isopropyl myristate, cetyl octanoate, octyl dodecyl myristate, isopropyl palmitate, butyl stearate, hexyl laurate, myristyl myristate, cetyl oleate, decyl oleate, hexyl decyl dimethyloctanoate, cetyl lactate, myristyl lactate, lanolin acetate, isocetyl stearate, isocetyl isostearate, isononyl isononanoate, cholesteryl 12-hydroxystearate, ethylene glycol di-2-ethylhexanoate, a dipentaerythritol fatty acid ester, N-alkyl glycol monoisostearate, neopentyl glycol dicaprate, diisostearyl malate, glycerin di-2-heptylundecanoate, trimethylolpropane tri-2-ethylhexanoate, trimethylolpropane triisostearate, pentaerythritol tetra-2-ethylhexanoate, glycerin tri-2-ethylhexanoate, glycerin trioctanoate, glycerin triisopalmitate, trimethylolpropane triisostearate, cetyl 2-ethylhexanoate, 2-ethylhexyl palmitate, glycerin trimyristate, glyceride tri-2-heptylundecanoate, a castor oil fatty acid methyl ester, oleyl oleate, acetoglyceride, 2-heptylundecyl palmitate, diisobutyl adipate, 2-octyldodecyl N-lauroyl-L-glutamate ester, di-2-heptylundecyl adipate, ethyl laurate, di-2-ethylhexyl sebacate, 2-hexyldecyl myristate, 2-hexyldecyl palmitate, 2-hexyldecyl adipate, diisopropyl sebacate, 2-ethylhexyl succinate, triethyl citrate, and combinations thereof, and
   0.3 wt % to 15 wt % of oil-soluble UV absorbers in liquid form including the octyl methoxycinnamate and the ultraviolet A absorber,
   wherein the weight ratio of phenylbenzimidazole sulfonic acid to 2-amino-2-methyl-1,3-propanediol is within the range of 4:1 to 2:1.

2. The water-in-oil type sunscreening cosmetic material according to claim 1, containing essentially no perfume other than 2-amino-2-methyl-1,3-propanediol.

* * * * *